(12) United States Patent
Johnson et al.

(10) Patent No.: US 10,005,704 B2
(45) Date of Patent: Jun. 26, 2018

(54) METHOD FOR PROLONGING A CATALYST'S LIFE DURING HYDROFLUORINATION

(71) Applicant: HONEYWELL INTERNATIONAL INC., Morristown, NJ (US)

(72) Inventors: Robert C. Johnson, Lancaster, NY (US); Daniel C. Merkel, Orchard Park, NY (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 0 days. days.

(21) Appl. No.: 14/604,867

(22) Filed: Jan. 26, 2015

(65) Prior Publication Data

US 2015/0152028 A1 Jun. 4, 2015

Related U.S. Application Data

(60) Division of application No. 12/825,040, filed on Jun. 28, 2010, now Pat. No. 8,952,208, which is a continuation-in-part of application No. 12/512,955, filed on Jul. 30, 2009, now Pat. No. 8,664,455.

(60) Provisional application No. 61/087,206, filed on Aug. 8, 2008.

(51) Int. Cl.
*C07C 17/25* (2006.01)
*C07C 17/087* (2006.01)
*C07C 17/20* (2006.01)
*C07C 19/10* (2006.01)
*C07C 21/18* (2006.01)

(52) U.S. Cl.
CPC ............ *C07C 17/25* (2013.01); *C07C 17/087* (2013.01); *C07C 17/20* (2013.01); *C07C 17/206* (2013.01); *C07C 19/10* (2013.01); *C07C 21/18* (2013.01)

(58) Field of Classification Search
None
See application file for complete search history.

(56) References Cited

U.S. PATENT DOCUMENTS 8,084,653 B2 * 12/2011 Tung .................. C07C 17/00
570/123
2007/0197842 A1 * 8/2007 Mukhopadhyay ...... C07C 17/00
570/155

FOREIGN PATENT DOCUMENTS

WO WO2007079431 * 7/2007

* cited by examiner

*Primary Examiner* — Clinton A Brooks
(74) *Attorney, Agent, or Firm* — Bruce O. Bradford

(57) ABSTRACT

The invention provides an improved process to manufacture 2-chloro-1,1,1,2-tetrafluoropropane (HCFC-244bb) by reacting 2-chloro-3,3,3,-trifluoropropene (HCFO-1233xf) with hydrogen fluoride, in the presence of a fluorination catalyst, where by using 2-chloro-3,3,3, -trifluoropropene (HCFO-1233xf) of high purity, the need to add an oxidizing agent (typically chlorine) to keep the catalyst active can be avoided. The HCFC-244bb is then used as an intermediate in the production of 2,3,3,3-tetrafluoropropene-1 (HFO-1234yf).

5 Claims, 1 Drawing Sheet

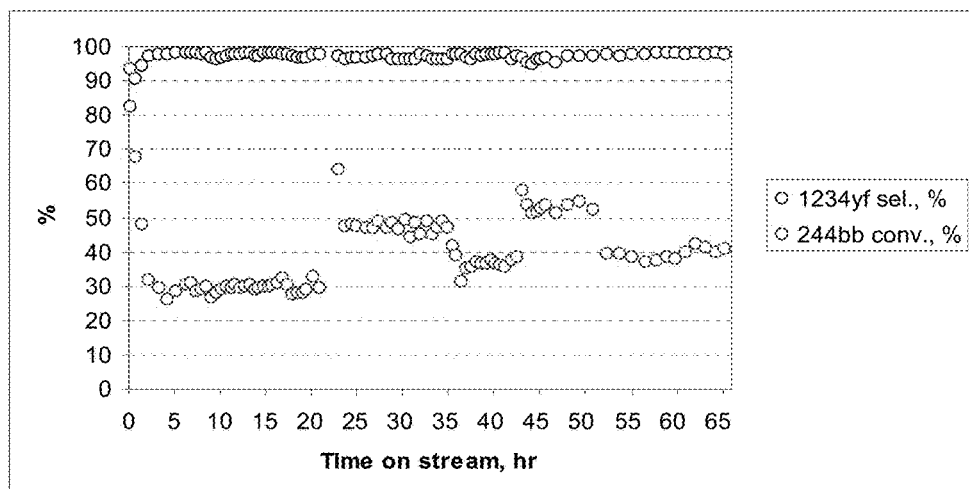

METHOD FOR PROLONGING A CATALYST'S LIFE DURING HYDROFLUORINATION

CROSS REFERENCES TO RELATED APPLICATIONS

This application is a division of U.S. Application Ser. No. 12/825,040, filed Jun. 28, 2010, which is a continuation-in part of U.S. application Ser. No. 12/512,955, filed Jul. 30, 2009, now U.S. Pat. No. 6,108,206, issued Mar. 4, 2014, which claims the priority benefit of United States provisional application number 61/087,206, filed Aug. 8, 2008, the contents of which are both incorporated herein by reference.

FIELD OF THE INVENTION

The present invention relates, generally, to methods for prolonging the life of a catalyst during hydrofluorination of an unsaturated material by maintaining the catalyst's valence in the active state.

BACKGROUND OF THE INVENTION

Fluorocarbon based fluids have found widespread use in industry in a number of applications, including refrigerants, aerosol propellants, blowing agents, heat transfer media, and gaseous dielectrics. Because of the suspected environmental problems associated with the use of some of these fluids, including the relatively high ozone depletion and global warming potentials, there is considerable interest in developing environmentally friendlier materials for such applications.

Tetrafluoropropenes, having zero ozone depletion and low global warming potential, have been identified as potentially filling this need. However, the toxicity, boiling point, and other physical properties in this class of chemicals vary greatly from isomer to isomer. One tetrafluoropropene having valuable properties is 2,3,3,3-tetrafluoropropene (HFO-1234yf). HFO-1234yf has been found to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

There is a continuing need for new and cost effective manufacturing processes for the production of such tetrafluoropropenes, particularly 2,3,3,3-tetrafluoropropene. It would be advantageous to have a process for the manufacture of HFO-1234yf that is continuous, and which uses readily available raw materials. As the prior art processes fail in one or more of these desirable features, more advantageous routes are desired, especially those amenable to large-scale manufacture.

In instant invention addresses each of these needs.

SUMMARY OF THE INVENTION

The present invention relates, generally, to an improved process for producing 2,3,3,3-tetrafluoropropene by improving the production of its process intermediate 2-chloro-1,1,1,2-tetrafluoropropane. More specifically, the present invention provides for a process of producing 2-chloro-1,1,1,2-tetrafluoropropane by reacting substantially pure 2-chloro-3,3,3,-trifluoropropene with hydrogen fluoride in the presence of a fluorination catalyst and without the need for continuous or intermittent catalyst regeneration.

It is common for the 2-chloro-3,3,3,-trifluoropropene intermediate feed material to contain underfluorinated intermediates and organic impurities, such as 2,3-dichloro-3,3-trifluoropropene. More specifically, in reactions where 2-chloro-3,3,3,-trifluoropropene is produced through the fluorination 1,1,2,3,-tetrachloropropene (HCC-1230xa) and/or 1,1,1,2,3-tetrachloropropane (HCC-240db), the reaction does not normally proceed completely to forming 2-chloro-3,3,3,-trifluoropropene. 2,3-dichloro-3,3-trifluoropropene is produced as an intermediate using an alternative reaction method. The inventors have discovered that the presence of this impurity causes gradual catalyst deactivation during the conversion of 2-chloro-3,3,3,-trifluoropropene to 2-chloro-1,1,1,2-tetrafluoropropane. To counteract such degradation, chlorine, or other similar oxidizing agents, may be added to keep the catalyst active. Thus, it increases costs associated with the production of the desired product, 2,3,3,3-tetrafluoropropene.

It was surprisingly discovered, however, that the addition of chlorine is not needed, so long as the 2-chloro-3,3,3,-trifluoropropene is of sufficiently high purity on an organic basis. This has the benefit of eliminating the cost of the oxidizing agent, all of the equipment needed for the addition of the oxidizing agent, the cost of separating the unreacted oxidizing agent, and the cost of disposing of any unwanted byproducts generated by the oxidizing agent. In the end, it also improves costs associated with 2,3,3,3-tetrafluoropropene production.

Accordingly, in one non-limiting embodiment, the instant invention relates to a process for the production of 2-chloro-1,1,1,2-tetrafluoropropane by reacting substantially pure 2-chloro-3,3,3,-trifluoropropene with hydrogen fluoride and a fluorination catalyst in the absence of an oxidizing agent. Substantially pure 2-chloro-3,3,3,-trifluoropropene includes a composition of at least 99% 2-chloro-3,3,3-trifluoropropene, or as otherwise defined herein. It may also include inorganic substrates, e.g. hydrogen fluoride, hydrogen chloride, etc., in any amount, which may be optionally used as a reaction co-feed.

Starting materials for the production of 2-chloro-3,3,3,-trifluoropropene may include any such materials which are known. As provided above, such starting materials, for example, may include 1,1,2,3,-tetrachloropropene and/or 1,1,1,2,3-tetrachloropropane, where 2-chloro-3,3,3,-trifluoropropene is produced by fluorinating one or both reactants. The resulting intermediate stream includes the product, 2-chloro-3,3,3-trifluoropropene, and one or more impurities, such as 2,3-dichloro-3,3-trifluoropropene. A substantially pure amount of 2-chloro-3,3,3-trifluoropropene, on an organic basis, is then obtained from the intermediate stream by separating the compound using known separation techniques, such as distillation.

The process may be conducted in a liquid phase or a vapor phase and continuously or batch-wise. Preferred, though non-limiting, mole ratios of hydrogen fluoride to substantially pure 2-chloro-3,3,3-trifluoropropene fed to the reaction ranges from at least 1:1 to about 50:1. The reaction may be conducted at a temperature of from about 30° C. to about 200° C. and a pressure of from about 5 psia to about 200 psia.

Fluorination catalysts may be selected from metal halides, halogenated metal oxides, neutral metals, metal alloys, activated carbon in bulk or supported form, or combinations thereof. In one embodiment, the fluorination catalyst is a liquid phase catalyst, which is selected from antimony halide, a tin halide, a tantalum halide, a titanium halide, a niobium halide, and molybdenum halide, an iron halide, a fluorinated chrome halide, a fluorinated chrome oxide, $SbCl_5$, $SbCl_3$, $SbF_5$, $SnCl_4$, $TaCl_5$, $TiCl_4$, $NbCl_5$, $MoCl_6$, $FeCl_3$, $CrF_3$, $Cr_2O_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, a fluorinated species of $Cr_2O_3$, or combinations thereof. In another embodiment, the fluorination catalyst is a vapor phase catalyst, which is selected from $Cr_2O_3$, $Cr_2O_3/Al_2O_3$, $Cr_2O_3/AlF_3$, $Cr_2O_3/$ carbon, $CoCl_2/Cr_2O_3/Al_2O_3$, $NiCl_2/Cr_2O_3/Al_2O_3$, $CoCl_2/AlF_3$, $NiCl_2/AlF_3$ or combinations thereof.

In another embodiment, the instant invention relates to a process for the production of 2,3,3,3-tetrafluoropropene by first reacting substantially pure 2-chloro-3,3,3,-trifluoropropene, on an organic basis, with hydrogen fluoride and a fluorination catalyst in the absence of an oxidizing agent to produce 2-chloro-1,1,1,2-tetrafluoropropane, and then dehydrohalogenating the 2-chloro-1,1,1,2-tetrafluoropropane under conditions effective to produce 2,3,3,3-tetrafluoropropene.

Substantially pure 2-chloro-3,3,3,-trifluoropropene, on an organic basis, includes at least 99% of 2-chloro-3,3,3-trifluoropropene, or as otherwise defined herein. It may also include inorganic substrates at any amount, e.g. hydrogen fluoride, hydrogen chloride, etc., which may be optionally used as a reaction co-feed.

Starting materials for the production of 2-chloro-3,3,3,-trifluoropropene may also include any other such materials which are known. For example, such starting materials may include 1,1,2,3,-tetrachloropropene and/or 1,1,1,2,3-tetrachloropropane, where 2-chloro-3,3,3, -trifluoropropene is produced by fluorinating one or both reactants. The resulting intermediate stream includes the product, 2-chloro-3,3,3-trifluoropropene, and one or more impurities, such as 2,3-dichloro-3,3-trifluoropropene. A substantially pure amount of 2-chloro-3,3,3-trifluoropropene is then obtained from the intermediate stream by separating the compound using known separation techniques, such as distillation.

In an even further embodiment, the instant invention relates to a process for producing 2,3,3,3-tetrafluoropropene by fluorinating 1,1,2,3,-tetrachloropropene and/or 1,1,1,2,3-tetrachloropropane to produce an intermediate stream comprising 2-chloro-3,3,3-trifluoropropene and one or more impurities. 2-chloro-3,3,3-trifluoropropene is then separated from the intermediate stream to form a substantially pure composition of 2-chloro-3,3,3-trifluoropropene on an organic basis, which is reacted with hydrogen fluoride and a fluorination catalyst in the absence of an oxidizing agent to produce 2-chloro-1,1,1,2-tetrafluoropropane. This product is then dehydrohalogenated under conditions effective to produce 2,3,3,3-tetrafluoropropene.

Additional embodiments and advantages will be readily apparent to one of ordinary skill in the art based the disclosure provided herein.

BRIEF DESCRIPTION OF THE FIGURE

FIG. 1 illustrates the selectivity of HFO-1234yf and conversion rate of HCFC-244bb with a feed of 95 GC %, 244bb/3.1GC %, 1233xf/0.35GC % 245cb; and 2.0 L of 10 wt % CsCl/90 wt % $MgF_2$ catalyst at a 1.0 lb/hr feed rate.

DETAILED DESCRIPTION OF THE INVENTION

The present invention relates, generally, to methods for prolonging the life of a catalyst during hydrofluorination of an unsaturated material and reducing the need for continuous or intermittent catalyst regeneration. In particular, the present invention relates to an improved process for producing 2,3,3,3-tetrafluoropropene (HCFC-1234yf) by improving the production of the reaction intermediate 2-chloro-1,1,1,2-tetrafluoropropane (HCFC-244bb). Production is specifically improved by first purifying the organic reactant 2-chloro-3,3,3,-trifluoropropene (HCFO-1233xf). This substrate is then reacted with hydrogen fluoride in the presence of a fluorination catalyst to form 2-chloro-1,1,1,2-tetrafluoropropane (HCFC-244b).

As set forth in U.S. Patent Application No. 2010/0036179, the contents of which are incorporated by reference herein, one process for producing 2-chloro-1,1,1,2-tetrafluoropropane (HCFC-244bb) requires reacting 2-chloro-3,3,3,-trifluoropropene (HCFO-1233xf) with hydrogen fluoride in the presence of a fluorination catalyst. The fluoride adds across the double bond in the HCFO-1233xf starting reagent, ultimately eliciting the haloalkane intermediate. HCFC-244bb is then used as a starting reagent in the production of 2,3,3,3-tetrafluoropropene (HFO-1234yf) which is well known in the art as described in U.S. Applications 20070007488, 20070197842, and 20090240090; the specifications of which are incorporated herein by reference.

In a method of preparing HCFO-1233xf, precursor reagents are fluorinated with hydrogen fluoride. This may be done, for example, by the gas or liquid phase catalytic fluorination of 1,1,2,3,-tetrachloropropene (HCC-1230xa) and/or 1,1,1,2,3-tetrachloropropane (HCC-240db) with HF to yield HCFO-1233xf. The reaction products of such precursors include HCFO-1233xf, unreacted HF, HCl, and other by-products.

One class of by-products includes underfluorinated intermediates and organic impurities (e.g. 2,3-dichloro-3,3-trifluoropropene, and structurally related compounds), which are produced because the reaction does not proceed to completion. While not intending to be bound by theory, it is believed that the presence of such organic impurities within the HCFO-1233xf co-feed results in catalyst degradation during the conversion to HCFC-244bb. To counteract such degradation, a continuous or batch wise addition of chlorine, or a similar oxidizing agent, is added as a co-feed to keep the catalyst active. It was surprisingly discovered, however, that this addition is not needed, so long as the HCFO-1233xf is of sufficiently high organic purity i.e. the other organic impurities are eliminated from the feed. This has the benefit of eliminating the cost of the oxidizing agent, all of the equipment needed for the addition of the oxidizing agent, the cost of separating the unreacted oxidizing agent, and the cost of disposing of any unwanted byproducts generated by the oxidizing agent.

As used herein, "sufficient purity" or "sufficiently high purity" or "high purity," on an organic basis, refers to any amount of purified HCFO-1233xf that does not degrade catalyst activity during conversion to HCFC-244bb. In one embodiment, HCFO-1233xf comprises greater than 99% of the organic portion of the composition. This feed may also include inorganic substrates, e.g. hydrogen fluoride, hydrogen chloride, etc., in any amount or weight percent, which may be optionally used as a reaction co-feed.

HCFO-1233xf may be produced using any method known in the art. For example, the reactor is preheated to the fluorination reaction temperature while anhydrous HF is fed to the reactor. 1,1,2,3,-tetrachloropropene (HCC-1230xa) and/or 1,1,1,2,3-tetrachloropropane (HCC-240db), as starting reagents, are fed to the reactor with hydrogen fluoride at any convenient temperature and pressure. In a preferred non-limiting embodiment, either or both of the HCC-1230xa or HCC-240db and the HF are pre-vaporized or preheated to a temperature of from about 30° C. to about 300° C. prior to entering the reactor. In another embodiment, the HCC-1230xa or HCC-240db and HF are vaporized in the reactor. In either case, the HF and HCC-1230xa or HCC-240db feeds are then adjusted to the desired mole ratio. The HF to HCC-1230xa or HCC-240db mole ratio preferably ranges from about 3:1 to about 100:1; more preferably from about 4:1 to about 50:1 and most preferably from about 5:1 to about 20:1.

The vapor phase fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. The vacuum pressure can be from about 5 torr (0.0966 psig) to about 760 torr (14.69 psig). During the vapor phase fluorination reaction, HCC-1230xa or HCC-240db and HF are reacted in a vapor phase in the presence of the fluorination catalyst. The reactant vapor is allowed to contact the fluorination catalyst for from about 1 to 120 seconds or more preferably from about 1 to 20 seconds. For purposes of this invention, "contact time" is the time required for the gaseous reactants to pass through the catalyst bed assuming that the catalyst bed is 100% void.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. Pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as using an oxidizing agent such as $O_2$ or chlorine. For example, passing air or air diluted with nitrogen over the catalyst at temperatures of from about 100° C. to about 400° C., preferably from about 200° C. to about 375° C., for from about 8 hours to about 3 days, depending on the size of the reactor.

HCFO-1233xf may be recovered from the fluorination product mixture, which includes HCFO-1233xf, unreacted starting materials, partially fluorinated intermediates and by-products (e.g. HCl and 2,3-dichloro-3,3-trifluoropropene). Recovery methods may include one or a combination of compound separation methods that are generally known in the art. In one non-limiting embodiment, HCFO-1233xf, some of the unreacted HF, and HCl are recovered as the distillate material in a distillation column, while unreacted organic starting materials, partially fluorinated intermediates and by-products, and some of the unreacted HF are recovered from the bottom of the column and recycled back to the fluorination reactor for further reaction. Such a method may be performed in a standard distillation column at a pressure which is less than about 300 psig, preferably less than about 200 psig and most preferably less than 150 psig. The pressure of the distillation column inherently determines the distillation operating temperature. The distillation column to recover the HCFO-1233xf, some of the unreacted HF, and HC 1 can be operated at a temperature from about −40° C. to about 100° C., preferably from about −40° C. to about 75° C. A second distillation optionally may be employed where the distillate portion includes substantially all the HCl. The column bottoms include sufficiently high purity, HCFO-1233xf and HF. HF can optionally be removed from this stream before entering the HCFC-244bb liquid phase fluorination reactor. HF can be removed from this stream by means known in the art including absorption with sulfuric acid, water, or reacting with a caustic solution.

Purified HCFO-1233xf may then be converted to HCFC-244bb using standard conversion techniques. In practice, a catalyst is charged in a fluorination reactor prior to heating the reactor. Then, the HF, HCl and the substantially pure HCFO-1233xf are fed to the reactor after the reactor reaches the desired temperature. Any reactor suitable for a fluorination reaction may be used in the invention. Preferably the reactor is constructed from materials which are resistant to the corrosive effects of HF such as Hastelloy-C, Inconel, Monel and fluoropolymer-lined vessels. Such liquid phase fluorination reactors are well known in the art.

The process of the invention may be carried out either in a batch or continuous mode. In a continuous process, the HCFO-1233xf, and HF are preferably fed simultaneously to the reactor after the reactor reaches the desired temperature. The temperature and pressure of the fluorination reaction remain essentially the same for both the batch and continuous modes of operation. The residence time or contact time, varies from about 1 second to about 2 hours, preferably from about 5 seconds to about 1 hour and most preferably from about 10 seconds to about 30 minutes. A sufficient quantity of catalyst must be present to effect the fluorination in the residence times described above. In a continuous mode of operation, HF, and HCFC-244bb are continuously removed from the reactor.

In the preferred embodiment, the reaction is conducted at a temperature of from about 30° C. to about 200° C., more preferably from about from about 50° C. to about 150° C., and still more preferably from about 75° C. to about 125° C. The liquid phase fluorination reaction is conducted with pressure in the reactor, as a consequence of the temperature needed for the reaction and the volatility of the materials involved. This pressure may vary depending on the temperature, quantity of hydrogen fluoride used, and conversion of HCFO-1233xf. Convenient operating pressures range from about 5 psia to about 200 psia, and preferably from 30 to about 175 psia, and most preferably about 60 psia to about 150 psia.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. $SbCl_5$ catalyst is preferred, though is non-limiting to the invention.

Alternatively, this reaction can be conducted using a vapor phase process, in which the reactor is filled with a vapor phase (solid) fluorination catalyst. Any fluorination catalysts known in the art may be used in this process. Of particular utility, though non-limiting to the invention, are vapor phase catalysts in which $SbCl_5$ is impregnated on carbon, and in which $SbCl_5$ is impregnated on $Al_2O_3$.

In one non-limiting embodiment the catalyst is an antimony halide. Antimony halide must be primarily available in the pentavalent state for it to remain active. This state gradually degrades to the trivalent state as a continuous halogen exchange reaction progresses. The addition of a strong oxidizing agent, such as elemental chlorine, was previously though to be necessary for the catalyst to remain active. In the halogen exchange, there is a complex formed between the HF and the pentavalent antimony ($Sb^{+V}$); this complex in turn interacts with the C—Cl bond on the organic moiety, resulting in a C—F organic bond (more favored thermodynamically), and a $Sb^V$—HCl complex; the HCl will quickly decouple from the complex, forming as a gaseous byproduct. The $Sb^{+V}$ remains available to form another active $Sb^{+V}$—HF complex in about 97% of these interactions, but in about 3% of these interactions, it degrades to the $Sb^{+III}$ state, which will not complex or be catalytically active. The instant invention illustrates that the presence of the $Sb^{+V}$ catalyst promotes the reaction, but the catalyst does not degrade to the inactive $Sb^{+III}$ form, if the feed is of sufficient purity to not contain materials which undergo the halogen exchange reaction mechanism.

In the preferred embodiment, the catalyst is present in an amount of from about 2% to about 80%, and preferably from about 5% to about 50%, and most preferably from about 10% to about 20%, based on the mole percent of HCFO-1233xf. Fluorination catalysts having a purity of at least 98% are preferred.

Based on reaction stoichiometry, the required mole ratio of HF to HCFO-1233xf is at least equal to the number of double bonds in the starting organic material and preferably is present in an excess. In the preferred embodiment, the mole ratio of HF to HCFO-1233xf ranges from at least about 1:1 to about 50:1, more preferably from about 1:1 to about 30:1 and most preferably from about 2:1 to about 15:1. Any water in the HF will react with and deactivate the catalyst. Therefore substantially anhydrous HF is preferred. By "substantially anhydrous" is meant that the HF contains less than about 0.03 weight % water and preferably contains less than about 0.01 weight % water. However, one of ordinary skill in the art will appreciate that the presence of water in the catalyst can be compensated for by increasing the amount of catalyst used. HF suitable for use in the reaction may be purchased from Honeywell International Inc. of Morristown, N.J.

The resulting HCFC-244bb, as well as HF may be recovered from the reaction mixture via any separation or purification method known in the art such as neutralization and distillation. The HCFC-244bb can be used in pure form, in a partially pure form, or impure form with the entire effluent from the HCFC-244bb production step as an intermediate in the production of 2,3,3,3-tetrafluoropropene HFO-1234yf.

To produce HFO-1234yf, the HCFC-244bb is introduced into the reactor as part of the reactor effluent from the preceding step. The HCFC-244bb may optionally be fed with an inert gas diluent such as nitrogen, argon, or the like. In a preferred, though non-limiting, embodiment, HCFC-244bb is pre-vaporized or preheated prior to entering the reactor. Alternatively, the HCFC-244bb is vaporized inside the reactor. Useful reaction temperatures may range from about 100° C. to about 700° C. Preferred temperatures may range from about 150° C. to about 600° C., and more preferred temperatures may range from about 200° C. to about 550° C. The reaction may be conducted at atmospheric pressure, super-atmospheric pressure or under vacuum. The vacuum pressure can be from about 5 torr (0.0966 psig) to about 760 torr (14.69 psig). Contact time of the HCFC-244bb with the catalyst may range from about 0.5 seconds to about 120 seconds, however, longer or shorter times can be used.

Conversion of HCFC-244bb to HFO-1234yf is at least about 10%, more preferably at least about 20%, and even more preferably at least about 30%. Preferably in such embodiments, the selectivity to HFO-1234yf, is at least about 70%, more preferably at least about 85% and more preferably at least about 95%.

In the preferred embodiment, the process flow is in the down or up direction through a bed of the catalyst. It may also be advantageous to periodically regenerate the catalyst after prolonged use while in place in the reactor. Regeneration of the catalyst may be accomplished by any means known in the art such as using an oxidizing agent such as $O_2$ or chlorine. For example, by passing air or air diluted with nitrogen over the catalyst at temperatures of from about 100° C. to about 400° C., preferably from about 200° C. to about 375° C., for from about 0.5 hour to about 3 days depending on the size of the reactor.

In general, the effluent from the dehydrohalogenation reaction step, including any intermediate effluents that may be present in multi-stage reactor arrangements, may be processed to achieve desired degrees of separation and/or other processing. For example, in embodiments in which the reactor effluent comprises HFO-1234yf, the effluent will generally also include HCl and unreacted HCFC-244bb. Some portion or substantially all of these components of the reaction product may be recovered from the reaction mixture via any separation or purification method known in the art such as absorption, neutralization and distillation. It is expected that unreacted HCFC-244bb could be recycled, completely or partially, to improve the overall yield of the desired $CF_3CF=CH_2$ (HFO-1234yf). Optionally but preferably, hydrogen chloride is then recovered from the result of the dehydrochlorination reaction. Recovering of hydrogen chloride is conducted by conventional distillation where it is removed from the distillate.

Alternatively, HCl can be recovered or removed by using water or caustic scrubbers. When a water extractor is used HCl is removed as an aqueous solution. When caustic is used, HCl is removed from system as a chloride salt in aqueous solution.

The catalysts may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and I. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported.

Useful examples of metal alloys include, but are not limited to, SS 316, Monel 400, Inconel 825, Inconel 600, and Inconel 625.

In an alternate embodiment of the invention, dehydrohalogenation of HCFC-244bb can also be accomplished by reacting it with a strong caustic solution that includes, but is not limited to KOH, NaOH, Ca(OH)$_2$ and CaO at an elevated temperature. In this case, the strength of the caustic solution is of from about 2 wt % to about 52 wt %, more preferably from about 5 wt % to about 50 wt % and most preferably from about 10 wt % to about 45 wt %. The caustic to HCFC-244bb mole ratio preferably ranges from about 1:1 to about 2:1; more preferably from about 1.1:1 to about 1.5:1 and most preferably from about 1.2:1 to about 1.4:1. The reaction may be conducted at a temperature of from about 20° C. to about 100° C., more preferably from about 30° C. to about 90° C. and most preferably from about 40° C. to about 80° C. As above, the reaction may be conducted at atmospheric pressure, super-atmospheric pressure or under vacuum. The vacuum pressure can be from about 5 torr (0.0966 psig) to about 760 torr (14.69 psig). In addition, a solvent or phase transfer catalyst such as Aliquat 336 may optionally be used to help dissolve the organic compounds in the caustic solution. This optional step may be conducted using solvents that are well known in the art for said purpose. Thereafter, HFO-1234yf may be recovered from the reaction product mixture comprised of unreacted starting materials and by-products by any means known in the art, such as by extraction and preferably distillation. The mixture of HFO-1234yf and any by-products are passed through a distillation column. For example, the distillation may be preferably conducted in a standard distillation column at atmospheric pressure, super-atmospheric pressure or a vacuum. Preferably the pressure is less than about 300 psig, preferably less than about 200 psig and most preferably less than 150 psig. The pressure of the distillation column inherently determines the distillation operating temperature. Preferably in such dehydrochlorination embodiments as described in this section, the conversion HCFC-244bb is at least about 60%, more preferably at least about 75%, and even more preferably at least about 90%. Preferably in such embodiments, the selectivity to HFO-1234yf, is at least about 70%, more preferably at least about 85% and more preferably at least about 94%.

In a preferred embodiment, the invention relates to a multistep process in which the above described process to produce HCFC-244bb is immediately preceded by a prior process step for producing 2-chloro-3,3,3,-trifluoropropene (HCFO-1233xf) by vapor phase fluorination of 1,1,2,3,-tetrachloropropene (HCC-1230xa) or 1,1,1,2,3-pentachloropropane (HCC-240db) with hydrogen fluoride to produce a stream comprising hydrogen fluoride, and 2-chloro-3,3,3,-trifluoropropene.

Based on the foregoing, the invention relates a process for the production of 2,3,3,3-tetrafluoropropene which comprises (i) reacting substantially pure 2-chloro-3,3,3,-trifluoropropene with hydrogen fluoride in the presence of a fluorination catalyst in the absence of an oxidizing agent to produce a composition comprising 2-chloro-1,1,1,2-tetrafluoropropane, then (ii) dehydrohalogenating the 2-chloro-1,1,1,2-tetrafluoropropane under conditions effective to produce 2,3,3,3-tetrafluoropropene.

In further embodiments, invention also provides a process for the production of 2,3,3,3-tetrafluoropropene which comprises a) fluorinating 1,1,2,3,-tetrachloropropene (HCC-1230xa) and/or 1,1,1,2,3-pentachloropropane to produce 2-chloro-3,3,3,-trifluoropropene and one or more organic impurities;

b) separating 2-chloro-3,3,3,-trifluoropropene from the organic impurities to form substantially pure 2-chloro-3,3,3,-trifluoropropene;

b) reacting substantially pure 2-chloro-3,3,3,-trifluoropropene with hydrogen fluoride and a fluorination catalyst in the absence of an oxidizing agent to produce a composition comprising 2-chloro-1,1,1,2-tetrafluoropropane; then c) dehydrohalogenating the 2-chloro-1,1,1,2-tetrafluoropropane under conditions effective to produce 2,3,3,3-tetrafluoropropene.

The following non-limiting examples serve to illustrate the invention.

EXAMPLES

Example 1

A continuous liquid phase fluorination of the 2-chloro-3,3,3-trifluoropropene (HCFO-1233xf)+HF→2-chloro-1,1,1,2-tetrafluoropropane (HCFC-244bb) is conducted, using as fluorination catalyst fluorinated SbCl$_5$.

Prior to the reaction, the 2-chloro-3,3,3-trifluoropropene (HCFO-1233xf) raw material [which had previously been prepared by vapor phase hydrofluorination reaction from 1,1,2,3, -tetrachloropropene (HCC-1230xa)] is distilled in a multi-stage distillation column under pressure to a purity in excess of 99%.

2230 grams of mixed antimony chlorides (5 moles SbCl$_5$ per 1 mole SbCl3) are added into a Teflon™-lined liquid phase reactor (Teflon is a trademark of E.I. duPont de Nemours & Co) equipped with a catalyst stripper, 2-inch ID (inside diameter) packed column and with a condenser whose function is to return entrained catalyst, some of the unreacted HF and some of the unreacted HCFO-1233xf to the reactor when the system is running in continuous reaction mode. The reactor is 2.75-inch ID×36-inch L (length) and is not equipped with a mixer/agitator. The reactor is heated to about 85° C.-87° C. The catalyst is then activated by the addition of about 700 grams of HF. HCl generated by the fluorination of the catalyst raises the reaction system pressure to about 100 psig where it is controlled. The continuous gaseous HF feed is started next. It is bubbled into the liquid catalyst through a dip tube at a rate of 1.1 lb/hr, and when 1.0 lbs of HF has been added, the purified 2-chloro-3,3,3-trifluoropropene feed is started also, through the same dip tube. The purified HCFO-1233xf is fed continuously at rates of about 1.0 lb/hr. The mole ratio of HF to 1233xf is 7.1:1. The reaction temperature is maintained at 85° C.-87° C. and the pressure is maintained at 100 psig. The product of the reaction, primarily HCFC-244bb, exits from the catalyst stripper, along with some excess HF as azeotrope. The experiment is run continuously for 120 hours. The average conversion of HCFO-1233xf for the run is >99% and the selectivity to 244bb reaches 98%. Throughout this run, no chlorine is added after the sixth hour—in prior runs (see Comparative Example) it had been necessary to make a batch wise chlorine addition every three-to-four hours.

Comparative Example

Prior operation in the same equipment, under the same operating conditions, but using as raw material feed a supply of 2-chloro-3,3,3-trifluoropropene (HCFO-1233xf) which had been similarly prepared, but not distilled or otherwise purified, and which contained organic impurities [principally 2,3-Dichloro-3,3-difluoropropene (HCFO-1232)]>3% required the addition of small quantities of chlorine (typically 20-30 grams for each 3-4 hours of operation); because this reaction involves both a halogen exchange reaction and hydrogen fluoride addition reaction mechanisms. In the absence of these additions, the activity of the catalyst would gradually degrade, such that the conversion of 2-chloro-3,3,3-trifluoropropene (HCFO-1233xf) into 2-chloro-1,1,1,2-tetrafluoropropane (HCFC-244bb) would gradually decrease and eventually cease altogether.

Example 2

This example illustrates the continuous vapor phase fluorination reaction of 1,1,2,3-tetrachloropropene (TCP)+ 3HF → 2-chloro-3,3,3-trifluoropropene (HCFO-1233xf)+ 3HCl. The fluorination catalyst for the experiment was fluorinated $Cr_2O_3$.

A continuous vapor phase fluorination reaction system consisting of N2, HF, and organic feed systems, feed vaporizer, superheater. 4" ID Monel reactor, acid scrubber, drier, and product collection system was used to study the reaction. The reactor was loaded with 9415.2 grams of pretreated $Cr_2O_3$ catalyst which equates to about 6.5 liters of catalyst. The reactor was then heated to a reaction temperature of about 235° C. with a N2 purge going over the catalyst after the reactor had been installed in a constant temperature sand bath. The reactor was at about 3 psig of pressure. HF feed was introduced to the reactor (via the vaporizer and superheater) as a co-feed with the N2 for 15 minutes when the N2 flow was stopped. The HF flow rate was adjusted to 1.4 lb/hr and then 1,1,2,3-tetrachloropropene (TCP) feed was started to the reactor (via the vaporizer and superheater). The feed rate of TCP was kept steady at about 0.8 lb/hr and HF feed was kept steady at 1.4 lb/hr for about a 15 to 1 mole ratio of HF to TCP. Once the reaction started the catalyst bed temperature rose to a range of 250-260° C. The contact time at 250-260° C., 3 psig and the above feed rates was calculated to be about 16 s. The average composition of the material that was collected over 500 hours of on-stream time was about 97.2 GC area % HCFO-1233xf, 1.6 GC area %244bb, 0.6 GC area % HFC-245cb, 0.4 GC area % 1232xf, 0.1 GC area % HCFC-1223xd, and 0.08 GC area % HCFO-1231xf, and 0.02 GC area % others. After 500 hours an under fluorinated intermediate, 2,3-dichloro-3,3-difluoropropene (HCFO-1232xf) started to appear as the selectivity to HCFO-1233xf decreased when the catalyst started losing activity. When the selectivity to HCFO-1233xf decreased to about 83% after 650 hours of on-stream time the reaction was stopped due to loss of catalyst activity. The conversion of TCP remained at >99% throughout the run.

Example 3

This example illustrates the continuous vapor phase dehydrochlorination reaction of 2-chloro-1,1,1,2-tetrafluoropropane (244bb)→2,3,3,3-tetrafluoropropene (1234yf)+HCl. The dehydrochlorination catalyst for the experiment was 10 wt % CsCl/90 wt % $MgF_2$.

Conversion of HCFC-244bb into HFO-1234yf was performed using a Monel reactor (ID 2 inch, length 32 inch) equipped with a Monel preheater (ID 1 inch, length 32 inch) which was filled with Nickel mesh to enhance heat transfer. The reactor was filled with 2.0 L of pelletized 10 wt % CsCl/90 wt % $MgF_2$ dehyrochlorination catalyst. Nickel mesh was placed at the top and at the bottom of reactor to support the catalyst. Multi-point thermocouple was inserted at the center of the reactor. The catalyst was pretreated in dry N2 flow for 6 hours at the temperature of 480° C. Then the feed with the composition 95GC % 244bb/3.1GC % 1233xf/ 0.35GC % 245cb was introduced into the reactor at the rate of 1.0 lb/hr. The feed vaporized prior entering the reactor preheater. The bottoms of the distillation column were discharged and recycled into the reactor. The feed rate was maintained constant at 1.0 lbs/hr and both temperature and pressure were varied. Temperature gradient throughout the reactor never exceeded 3-5° C. The productivity of the catalyst was estimated at 3-6 lbs/hr/ft$^3$. The highest productivity was observed at 470° C. and 45 psig, and the lowest productivity was observed at 480° C. and 3 psig pressure. The reaction products were fed into the caustic scrubber to remove HCl by-product. Then the product stream was passed through a column filled with desiccant to remove residual moisture. An oilless compressor was used to feed crude product into the distillation column that was maintained at 30-45 psig pressure. Distillation was performed in a continuous mode and the take-off rate was equal to the rate of production of HFO-1234yf in the reactor. The purity of distilled 1234yf was 99.9GC %+. GC analysis of the distillate shows presence of light impurities with a ppm level of heavy impurities.

480° C. at 3 psig—244bb conversion~30%, Selectivity to 1234yf~97%
480° C. at 20 psig—244bb conversion~47%, Selectivity to 1234yf~96%
470° C. at 20 psig—244bb conversion~36%, Selectivity to 1234yf~97%
470° C. at 45 psig—244bb conversion~53%, Selectivity to 1234yf~96%
460° C. at 45 psig—244bb conversion~38%, Selectivity to 1234yf~98%

Reaction data. Conditions: Feed 95GC % 244bb/3.1GC % 1233xf/0.35GC % 245cb;
2.0 L of 10 wt % CsCl/90 wt % $MgF_2$ catalyst; 1.0 lb/hr feed rate.

| Time on-stream (hrs.) | conversion of 244bb (%) | Selectivity to 1234yf (%) | Temperature (° C.) | Pressure (psig) |
|---|---|---|---|---|
| 0.25 | 93.30 | 82.42 | 484.30 | 3.00 |
| 0.80 | 67.61 | 90.38 | 489.00 | 3.90 |
| 1.43 | 47.78 | 94.14 | 479.80 | 3.50 |
| 2.27 | 31.98 | 97.34 | 479.80 | 3.40 |
| 3.32 | 29.36 | 97.70 | 478.80 | 3.80 |
| 4.32 | 26.24 | 97.56 | 478.70 | 2.80 |
| 5.23 | 28.45 | 97.88 | 480.30 | 2.90 |
| 6.20 | 30.53 | 98.01 | 480.30 | 3.20 |
| 6.80 | 30.91 | 98.13 | 478.40 | 3.30 |
| 7.37 | 28.36 | 97.88 | 478.80 | 2.90 |
| 7.93 | 29.01 | 97.84 | 479.30 | 3.10 |
| 8.48 | 29.95 | 97.91 | 478.30 | 3.30 |
| 9.05 | 26.61 | 96.76 | 479.60 | 2.70 |
| 9.62 | 27.98 | 96.12 | 476.80 | 2.90 |
| 10.20 | 28.84 | 96.66 | 480.20 | 3.00 |
| 10.70 | 29.70 | 97.16 | 480.50 | 3.10 |
| 11.22 | 29.30 | 97.62 | 480.30 | 3.30 |
| 11.72 | 30.47 | 97.65 | 480.70 | 3.30 |
| 12.25 | 29.57 | 97.59 | 480.30 | 3.30 |
| 12.75 | 29.83 | 97.92 | 480.00 | 3.50 |
| 13.27 | 30.10 | 98.23 | 479.60 | 2.80 |
| 13.78 | 28.73 | 97.02 | 480.10 | 2.80 |
| 14.28 | 29.54 | 97.31 | 480.80 | 2.90 |
| 14.80 | 29.95 | 98.05 | 479.80 | 2.90 |
| 15.30 | 29.71 | 97.98 | 480.60 | 3.00 |
| 15.80 | 30.50 | 98.14 | 480.80 | 2.90 |
| 16.32 | 30.68 | 97.96 | 481.50 | 3.10 |
| 16.83 | 32.21 | 97.79 | 482.50 | 3.10 |

-continued

| Time on-stream (hrs.) | conversion of 244bb (%) | Selectivity to 1234yf (%) | Temperature (° C.) | Pressure (psig) |
| --- | --- | --- | --- | --- |
| 17.35 | 30.37 | 97.68 | 478.00 | 3.20 |
| 17.85 | 27.67 | 97.18 | 479.20 | 3.30 |
| 18.40 | 28.06 | 96.50 | 477.50 | 3.20 |
| 18.95 | 27.84 | 96.58 | 478.20 | 3.40 |
| 19.50 | 28.85 | 96.66 | 482.30 | 3.40 |
| 20.18 | 32.52 | 97.55 | 480.00 | 3.40 |
| 20.87 | 29.15 | 97.47 | 480.10 | 3.20 |
| 22.90 | 64.16 | 97.20 | 478.90 | 17.40 |
| 23.65 | 47.32 | 96.23 | 477.80 | 17.50 |
| 24.32 | 47.80 | 96.81 | 478.60 | 17.00 |
| 25.00 | 47.45 | 96.83 | 479.40 | 16.90 |
| 26.02 | 47.10 | 96.84 | 479.50 | 18.50 |
| 26.78 | 46.99 | 97.34 | 478.60 | 20.00 |
| 27.38 | 48.61 | 97.45 | 478.80 | 20.00 |
| 28.22 | 47.00 | 97.41 | 477.80 | 20.00 |
| 28.93 | 48.53 | 96.40 | 480.00 | 20.00 |
| 29.63 | 46.61 | 96.10 | 477.70 | 20.00 |
| 30.23 | 49.28 | 96.14 | 480.80 | 20.00 |
| 30.83 | 44.30 | 96.11 | 477.70 | 20.00 |
| 31.45 | 48.53 | 96.18 | 479.50 | 20.00 |
| 32.05 | 45.03 | 97.45 | 477.70 | 20.00 |
| 32.72 | 48.94 | 97.09 | 480.10 | 20.00 |
| 33.30 | 45.10 | 96.24 | 478.00 | 20.00 |
| 33.83 | 46.72 | 96.25 | 479.70 | 20.00 |
| 34.37 | 49.04 | 96.21 | 479.30 | 20.00 |
| 34.90 | 46.86 | 96.34 | 477.80 | 20.00 |
| 35.42 | 41.57 | 97.52 | 474.60 | 20.00 |
| 35.95 | 38.83 | 97.44 | 469.40 | 20.00 |
| 36.48 | 31.20 | 97.45 | 468.40 | 20.00 |
| 37.02 | 34.86 | 96.45 | 470.10 | 20.00 |
| 37.55 | 35.41 | 96.44 | 470.20 | 20.00 |
| 38.07 | 37.17 | 97.71 | 469.90 | 20.00 |
| 38.63 | 36.72 | 97.31 | 471.10 | 20.00 |
| 39.15 | 36.66 | 97.68 | 470.00 | 20.00 |
| 39.67 | 37.41 | 97.85 | 470.80 | 20.00 |
| 40.20 | 36.43 | 97.86 | 469.40 | 20.00 |
| 40.73 | 36.10 | 97.98 | 469.20 | 20.00 |
| 41.27 | 35.34 | 97.97 | 470.50 | 20.00 |
| 42.05 | 37.63 | 96.08 | 472.00 | 20.00 |
| 42.57 | 38.60 | 97.20 | 470.30 | 20.00 |
| 43.12 | 57.72 | 96.75 | 469.60 | 45.00 |
| 43.65 | 53.72 | 95.42 | 467.10 | 45.00 |
| 44.17 | 51.28 | 94.83 | 468.70 | 45.00 |
| 44.68 | 51.60 | 96.39 | 467.50 | 45.00 |
| 45.20 | 52.52 | 96.36 | 469.80 | 45.00 |
| 45.72 | 53.43 | 96.65 | 468.90 | 45.00 |
| 46.77 | 51.14 | 95.44 | 468.50 | 45.00 |
| 48.15 | 53.38 | 97.23 | 470.70 | 45.00 |
| 49.32 | 54.53 | 97.21 | 470.90 | 45.00 |
| 50.88 | 51.94 | 97.21 | 469.40 | 45.00 |
| 52.35 | 39.24 | 97.70 | 459.60 | 45.00 |
| 53.75 | 39.15 | 97.19 | 459.30 | 45.00 |
| 55.03 | 38.45 | 97.63 | 458.30 | 45.00 |
| 56.57 | 37.19 | 97.61 | 457.50 | 45.00 |
| 57.85 | 37.44 | 97.88 | 458.90 | 45.00 |
| 58.93 | 38.18 | 97.91 | 458.80 | 45.00 |
| 59.98 | 37.98 | 98.04 | 460.10 | 45.00 |
| 61.05 | 39.77 | 97.43 | 463.00 | 45.00 |
| 62.10 | 42.11 | 97.92 | 462.20 | 45.00 |
| 63.20 | 41.11 | 97.74 | 459.10 | 45.00 |
| 64.27 | 39.64 | 98.05 | 460.60 | 45.00 |
| 65.32 | 40.98 | 97.70 | 461.40 | 45.00 |

We claim:

1. A process for the production of 2,3,3,3-tetrafluoropropene comprising:
  (i) fluorination of a starting material comprising 1,1,2,3-tetrachloropropene and/or 1,1,1,2,3-pentachloropropane with hydrogen fluoride to produce an intermediate stream comprising 2-chloro-3,3,3-trifluoropropene and 2,3-dichloro-3,3-difluoropropene;
  (ii) purifying the intermediate stream comprising 2-chloro-3,3,3-trifluoropropene to produce a feed stream comprising at least 99% by weight of 2-chloro-3,3,3-trifluoropropene based on the organics in the feed stream;
  (iii) reacting the feed stream comprising at least 99% by weight of 2-chloro-3,3,3-trifluoropropene based on the organics in the feed stream with hydrogen fluoride and a fluorination catalyst in the absence of an oxidizing agent to produce 2-chloro-1,1,1,2-tetrafluoropropane; and
  (iv) dehydrohalogenating the 2-chloro-1,1,1,2-tetrafluoropropane under conditions effective to produce 2,3,3,3-tetrafluoropropene.

2. The process of claim 1 wherein the feed stream is produced by a process comprising fluorinating 1,1,2,3,-tetrachloropropene and/or 1,1,1,2,3-tetrachloropropane and separating 2-chloro-3,3,3-trifluoropropene from an intermediate stream comprising 2-chloro-3,3,3-trifluoropropene and one or more impurities.

3. The process of claim 2 wherein said at least one impurity is 2,3-dichloro-3,3-trifluoropropene.

4. The process of claim 2 wherein the step of separating 2-chloro-3,3,3-trifluoropropene from one or more impurities is performed by distillation.

5. A process for producing 2,3,3,3-tetrafluoropropene comprising
  (i) fluorinating 1,1,2,3,-tetrachloropropene and/or 1,1,1,2,3-tetrachloropropane to produce an intermediate stream comprising 2-chloro-3,3,3-trifluoropropene and 2,3-dichloro-3,3-difluoropropene;
  (ii) separating 2-chloro-3,3,3-trifluoropropene from the intermediate stream by distillation to form a feed stream comprising at least about 99% by weight of organics of 2-chloro-3,3,3-trifluoropropene;
  (iii) reacting said feed stream with hydrogen fluoride and a fluorination catalyst in the absence of an oxidizing agent to produce 2-chloro-1,1,1,2-tetrafluoropropane; and
  (iv) dehydrohalogenating the 2-chloro-1,1,1,2-tetrafluoropropane under conditions effective to produce 2,3,3,3-tetrafluoropropene.

* * * * *